United States Patent [19]

Moseley

[11] Patent Number: 4,906,188
[45] Date of Patent: Mar. 6, 1990

[54] DRY FIELD TONGUE GUARD

[76] Inventor: Daryl F. Moseley, 15901 W. Nine Mile #506, Southfield, Mich. 48075

[21] Appl. No.: 349,321

[22] Filed: May 8, 1989

[51] Int. Cl.⁴ ............................................. A61C 17/04
[52] U.S. Cl. ...................................................... 433/93
[58] Field of Search .................................... 433/93, 94

[56] References Cited

U.S. PATENT DOCUMENTS 2,603,870 7/1952 Nordin .................................. 433/93
4,781,587 11/1985 Kubo ..................................... 433/93

Primary Examiner—Robert Peshock

[57] ABSTRACT

A disposable dry field tongue guard for intra-oral placement during a dental procedure to remove saliva from around the lingual side of the lower arch while also constraining the tongue so that the tongue does not interfere with the procedure. The dry field tongue guard comprises an evacuation tube having an exterior end that connects to a suction source. The interior end of the tube fits into an aperture that is centrally located in a curvatured top wall of a tongue guard sheath. There is a cavity within the tongue guard sheath within which the interior tip end of the evacuation tube is located. Channels extend from this cavity downwardly and outwardly to the outer periphery of the tongue guard sheath. A tongue shield for fitting over the tongue is disposed beneath the tongue guard shield. The device is retained in place on a patient during a dental procedure by means of a chin blade that has a friction lock fit on the exterior end of the evacuation tube.

3 Claims, 1 Drawing Sheet

DRY FIELD TONGUE GUARD

BACKGROUND AND SUMMARY OF THE INVENTION

This invention relates generally to dental equipment, and more specifically it relates to a device that can be used by a dentist to facilitate the performance of a dental procedure. The invention is a dry field tongue guard that that is placed intra-orally to draw saliva from the mouth so that the saliva does not accumulate and interfere with a procedure that is being performed by the dentist.

Many dental procedures require the removal of saliva from the mouth so that the saliva does not interfere with the procedures. Saliva ejectors are therefore standard pieces of dental office equipment. A typical saliva ejector is in the form of a hook-shaped tube. One end of the saliva ejector is connected to a flexible suction tube while the opposite end is placed in the mouth. The hook-shape allows the ejector to hang over the lower lip and into the mouth. Saliva is sucked out of the mouth and carried away.

It is important in many procedures to have a saliva ejector which can be effective over a relatively large area, and this is one of the objectives of the present invention. It is also often important for a saliva ejector to be effective in keeping the tongue from interfering with the area of the mouth in which a procedure is being performed, and this is another objective of the invention. The present invention relates to a dry field tongue guard that is effective to suck saliva from a comparatively large area of the mouth while at the same time keeping the tongue from interfering with a dental procedure.

The dry field tongue guard of the present invention also possesses the ability to be quickly and reliably adjusted to a patient's mouth when put to use, and it also has the ability to be quickly and conveniently removed after use. Briefly, the preferred embodiment of the invention comprises in combination, an evacuation tube that may be somewhat hook-shaped, a tongue guard that is fitted onto the interior end of the evacuation tube, a tongue sheath that fits over the tongue and coacts with the tongue guard, and a chin blade that is fitted onto the exterior end of the evacuation tube and engages the underside of the chin to keep the dry field tongue guard in place in the mouth. The dry field tongue guard may be fabricated in different sizes to accommodate different size mouths such as adult and children.

The foregoing features, advantages, and benefits of the invention will be seen in the ensuing description and claims which should be considered in conjunction with the accompanying drawings. The drawings disclose a preferred embodiment of the invention in accordance with the best mode contemplated at the present time in carrying out the invention.

DESCRIPTION OF THE PREFERRED EMBODIMENT

Figure 1:
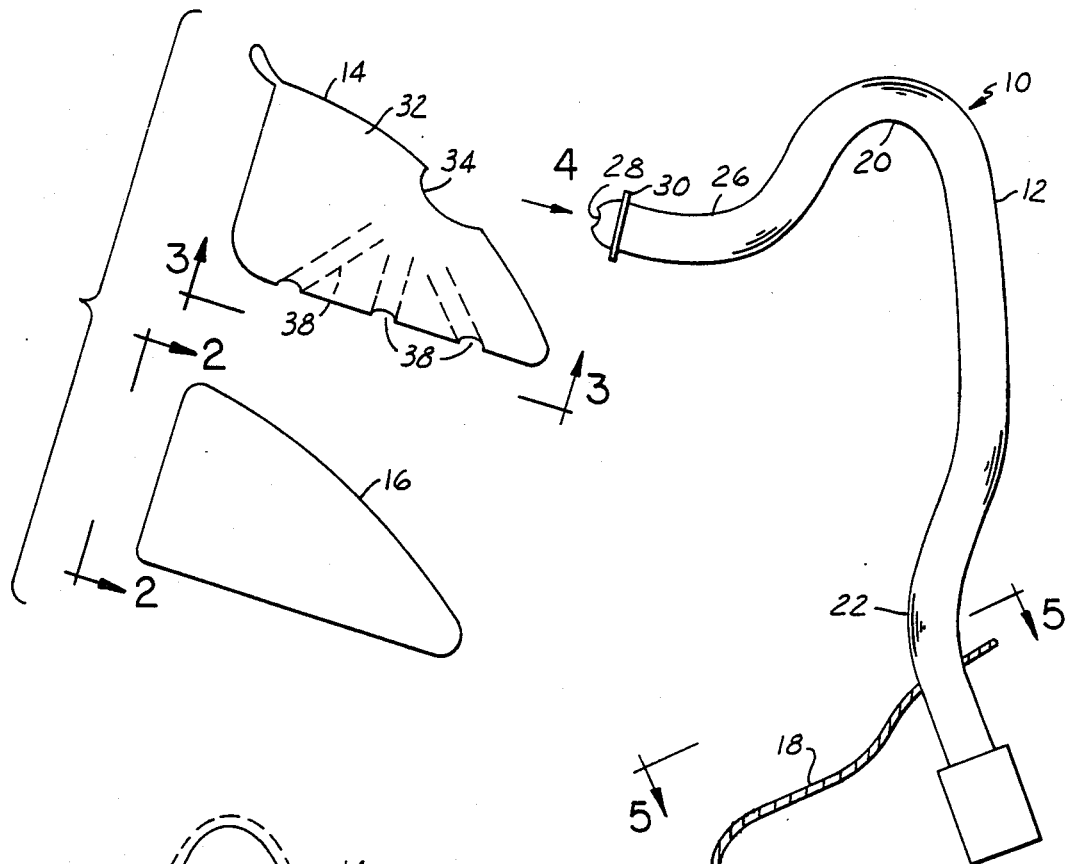
FIG. 1 is a side view in exploded form of the dry field tongue guard of the invention.
Figure 2:
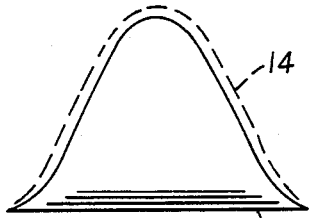
FIG. 2 is a view taken in the direction of arrows 2—2 in FIG. 1.
Figure 4:
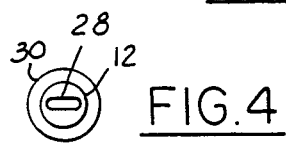
FIG. 4 is a view taken in the direction of arrow 4 in FIG. 1.
Figure 3:
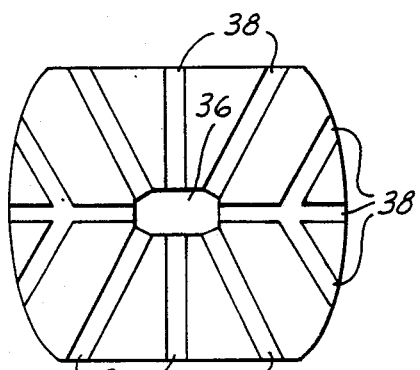
FIG. 3 is a view taken in the direction of arrows 3—3 in FIG. 1.
Figure 5:
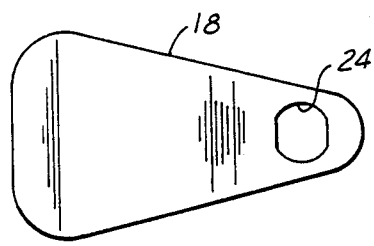
FIG. 5 is a view taken in the direction of arrows 5—5 in FIG. 1.

As shown in FIG. 1, the dry field tongue guard 10 comprises an evacuation tube 12, a tongue guard sheath 14, a tongue shield 16, and a chin blade 18.

Evacuation tube 12 is preferably a firm plastic tube formed to the illustrated shape which includes a hook-shaped portion 20 for fitting over the lower lip and front teeth of the lower arch. The exterior end of tube 12 is designated 22, and it is onto this exterior end that chin blade 18 is fitted. The chin blade has a hole 24 through which tube 12 passes. This allows the chin blade to be slid up and down exterior end portion 22. The fit of the tube within the hole however forms a friction lock that keeps the chin blade stable when the chin blade is disposed to engage the underside of a patient's chin when the dry field tongue guard is in place.

The interior end of tube 12 is designated by the numeral 26, and this end comprises an oval shaped opening 28 at the very end. Just behind this opening 28 is a flange, or lip, 30. It is this end 26 of tube 12 that is separably snap-fitted to tongue guard sheath 14.

The tongue guard sheath comprises a curvatured wall 32 with a centrally located aperture 34. This aperture is shaped to fit onto the end 26 of tube 12. The tongue guard sheath is preferably constructed of a thermoplastic material for moldability in hot water.

Within sheath 14 at aperture 34 is a cavity 36. When the sheath is fitted onto tube 12, hole 28 is located within this cavity. The interior of the sheath is configured with several channels 38 that are in communication with cavity 36. These channels radiate generally downwardly and outwardly from the cavity to the outer edge of the sheath. The channels may be straight or may include branches.

Tongue shield 16 has a shape that is configured to fit to the underside of sheath 14, but without blocking flow through channels 38. It is also shaped to fit over the patient's tongue and is preferably of a thermoplastic material for moldability to conform to the patient's tongue size and shape.

When the dry field tongue guard has been assembled and positioned in a patient's mouth, it is effective to draw saliva from a large area while constraining the patient's tongue. Specifically, the suction force that is applied through tube 12 is delivered to cavity 36. The suction force is in turn transmitted through channels 38 to a number of points around the lingual side of the lower arch. Saliva that is present at any of these points will be sucked up through the channels 38 and into cavity 36. From there, the saliva will enter tube 12 at hole 28 and pass through the tube to end 22 which is connected to a flexible hose (not shown) leading to a suction source.

The design of of the chin blade coupled with the attachment thereof to tube 12 enables the dry field tongue guard to be conveniently fitted to a patient for use, and to be conveniently removed from the patient after use. Moreover, the design is such that a stable placement of the dry field tongue guard can be obtained. The dry field tongue guard is effective to draw saliva from a large area of the mouth while preventing the tongue from interfering with a dental procedure.

While a preferred embodiment of the invention has been disclosed, it will be appreciated that principles are applicable to other embodiments.

What is claimed is:

1. A disposable dry field tongue guard for intra-oral usage comprising an evacuation tube including a hook-shaped section that allows the tube to hang over the lower lip and arch as passes into the oral cavity, said tube passing to the lingual side of the arch and having an interior end that projects generally toward the rear of the mouth and includes a hole, a tongue guard sheath having a curvatured top wall containing an aperture in a central region thereof, said interior end of said tube fitting into said aperture so that the hole in said interior end of said tube is disposed inwardly of said tongue guard sheath, said tongue guard sheath having a cavity interior of said aperture, and said hole in said interior tube end being disposed within said cavity, said tongue guard sheath having a number of channels formed interiorly of said curvatured top wall that begin at said cavity and radiate downwardly and outwardly from said cavity to a peripheral edge portion of said tongue guard sheath, said channels extending to both the right and left sides of the arch, a tongue shield for fitting over the tongue and that underlies and cooperates with said tongue guard sheath and the channels therein so that suction force delivered by said tube is communicated through said cavity and said channels to the peripheral edge portion of said tongue guard sheath on both right and left sides of the arch, and a chin blade that is fitted in an adjustable manner on the exterior end of said tube so that the dry field tongue guard can be intra-orally positioned and retained in such a manner that the tongue guard sheath and the tongue shield constrain the tongue while saliva can be evacuated from around the interior of the lower arch by being sucked through said channels, said cavity, and said evacuation tube.

2. A disposable dry field tongue guard as set forth in claim 1 in which the chin blade has a hole through which the evacuation tube passes, the chin blade is moveable along the evacuation to to provide for adjustment of the chin blade when the dry field tongue guard is being intra-orally positioned in a patient's mouth, yet the chin blade also has a friction lock on the evacuation tube when the dry field tongue guard has been positioned so that the dry field tongue guard remains in intra-oral position during a dental procedure.

3. A disposable dry field tongue guard as set forth in claim 1 in which certain of said channels have branches.

* * * * *